United States Patent [19]
Kinsinger et al.

[11] Patent Number: 5,545,230
[45] Date of Patent: Aug. 13, 1996

[54] PROSTHESIS MOUNTING ADAPTER AND METHOD

[75] Inventors: Jay H. Kinsinger, Cedarville; Robert E. Arbogast; James W. Capper, both of Mount Sterling; James M. Colvin, Hilliard, all of Ohio

[73] Assignee: Ohio Willow Wood Company, Mount Sterling, Ohio

[21] Appl. No.: 320,641

[22] Filed: Oct. 11, 1994

[51] Int. Cl.$^6$ .................... A61F 2/80; A61F 2/62; F16B 37/08
[52] U.S. Cl. .................... 623/38; 623/55; 411/432; 411/537; 403/12
[58] Field of Search ............... 623/55, 53, 52, 623/49, 48, 45, 40, 38, 27; 433/167, 171, 172, 196; 411/537, 546, 432, 258, 429, 373, 377, 553, 84, 85; 403/11, 12, 21, 22, 267, 268, 87, 84, 110

[56] References Cited

U.S. PATENT DOCUMENTS

| | | | |
|---|---|---|---|
| 529,683 | 11/1894 | Herman | 411/429 |
| 1,253,573 | 1/1918 | Burke | 411/429 |
| 2,141,071 | 12/1938 | Sorensen | 411/258 |
| 3,206,235 | 9/1965 | Albinson et al. | 623/38 |
| 3,749,362 | 7/1973 | O'Connor et al. | 411/537 |
| 4,227,722 | 10/1980 | Barber | 411/84 |
| 4,710,082 | 12/1987 | Curtis | 411/429 |
| 5,033,924 | 7/1991 | Cosenza | 411/282 |
| 5,047,063 | 9/1991 | Chen | 623/38 |
| 5,167,465 | 12/1992 | Inui et al. | 403/317 |
| 5,249,899 | 10/1993 | Wilson | 411/82 |

FOREIGN PATENT DOCUMENTS

| | | | |
|---|---|---|---|
| 1800500 | 5/1970 | Germany | 623/38 |
| 1465045 | 3/1989 | U.S.S.R. | 623/53 |
| 2162069 | 1/1986 | United Kingdom | 623/38 |
| 93017640 | 9/1993 | WIPO | 623/38 |

OTHER PUBLICATIONS

Flex-Foot Inc. (Two Brochures), 1993.

*Primary Examiner*—David Isabella
*Assistant Examiner*—Laura Fossum
*Attorney, Agent, or Firm*—Oblon, Spivak, McClelland, Maier & Neustadt, P.C.

[57] ABSTRACT

An adapter assembly which is particularly advantageous in allowing for adjusting and positioning of prosthetic devices which are attached to a stump or stump socket. The adapter is particularly advantageous for orienting and positioning of a Symes prosthesis, due to the small space requirements. In accordance with a preferred embodiment, an interface member is attached to a stump socket, with a nut movably disposed inside of a cavity of the interface member. The nut includes an aperture extending therethrough, and receives a hollow laminating bolt which clamps the prosthesis and adapter assembly in place to allow the user to test the prosthesis. If adjustments are needed, the hollow bolt can be loosened, and adjustments performed via the movably disposed nut. Once a desired position is achieved, a resin is injected through the laminating bolt and into the cavity of the interface. After the resin has hardened or cured, the hollow laminating bolt is replaced with a solid bolt.

40 Claims, 5 Drawing Sheets

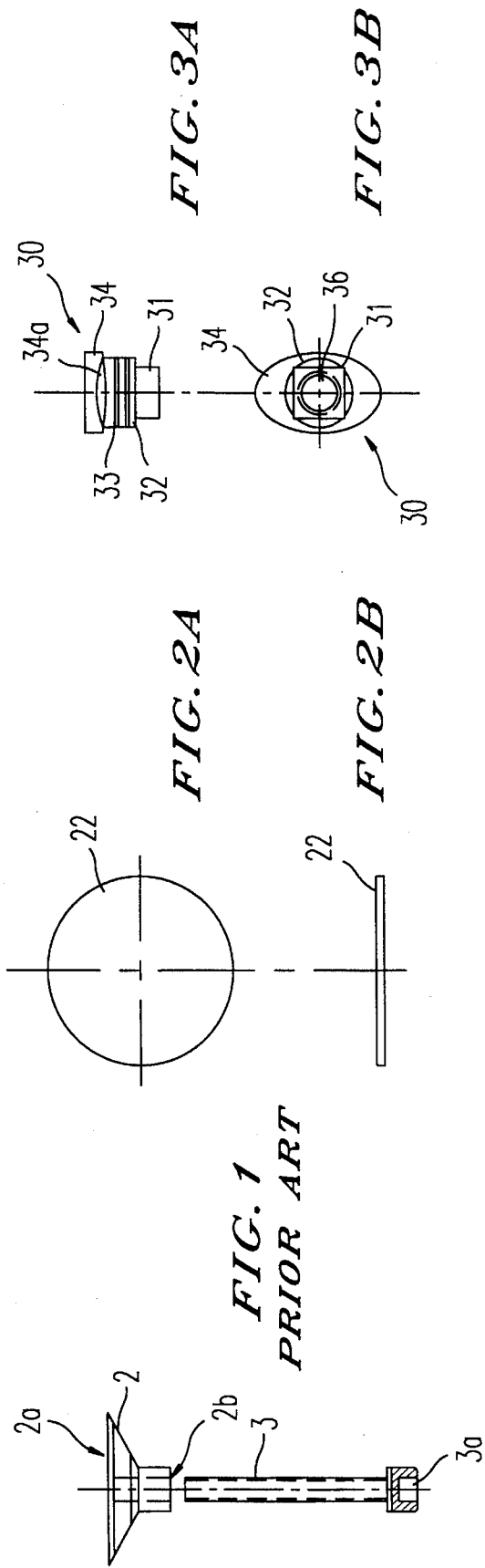

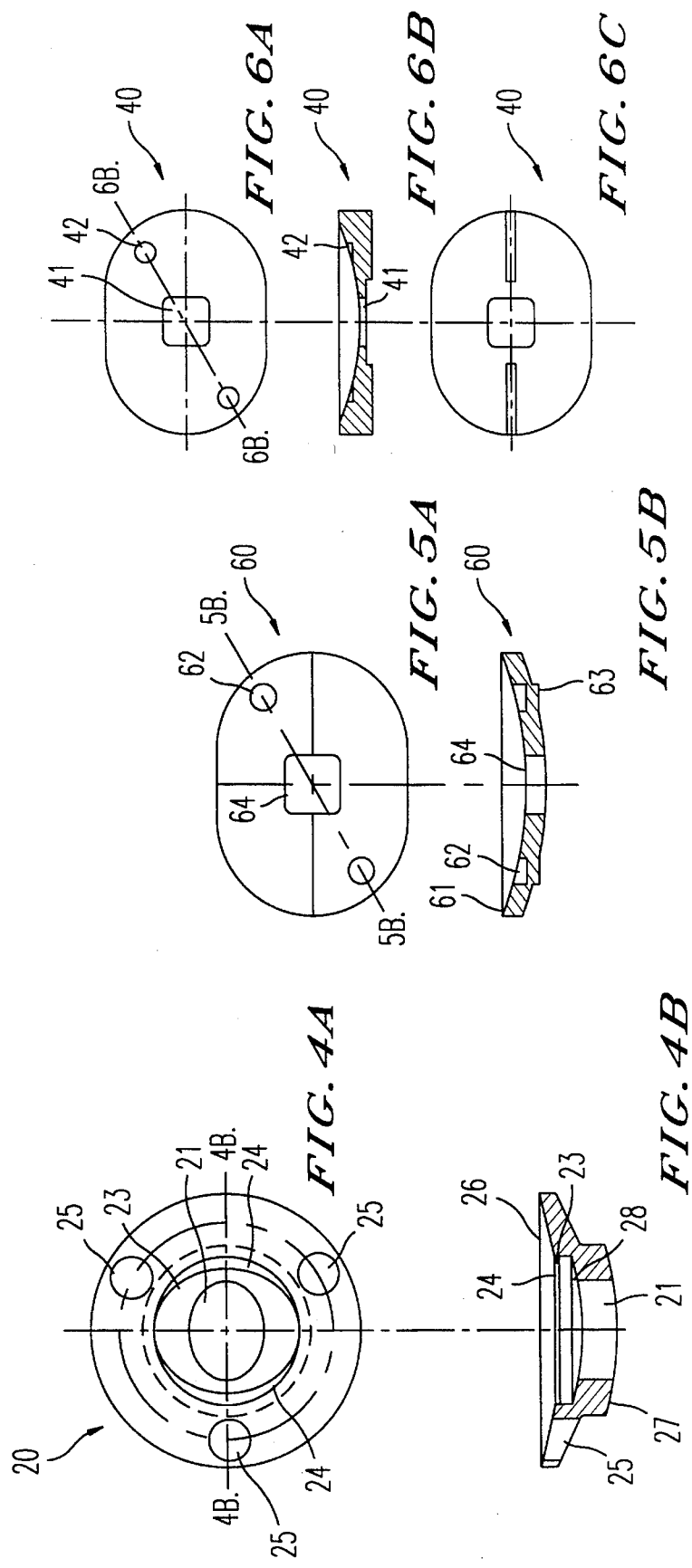

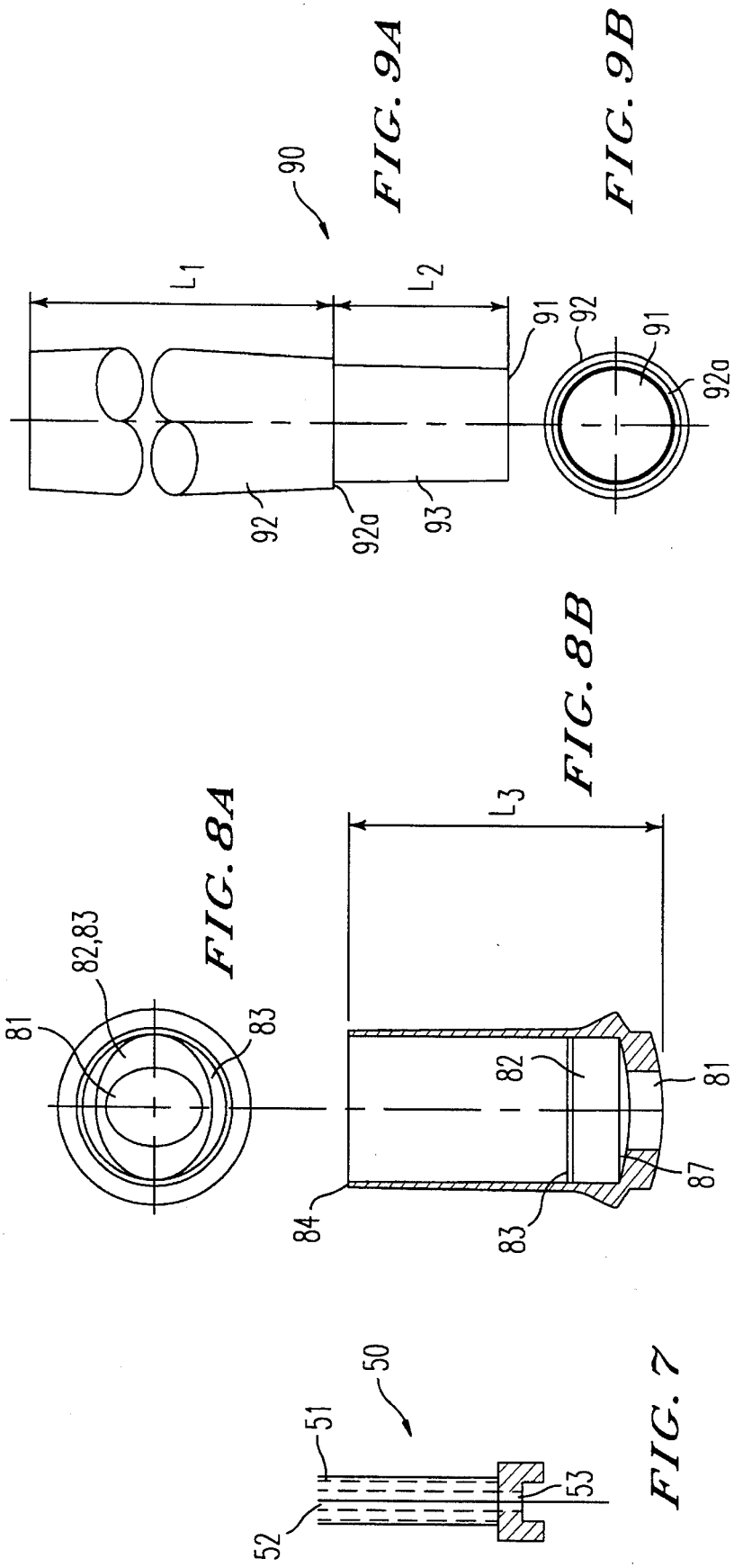

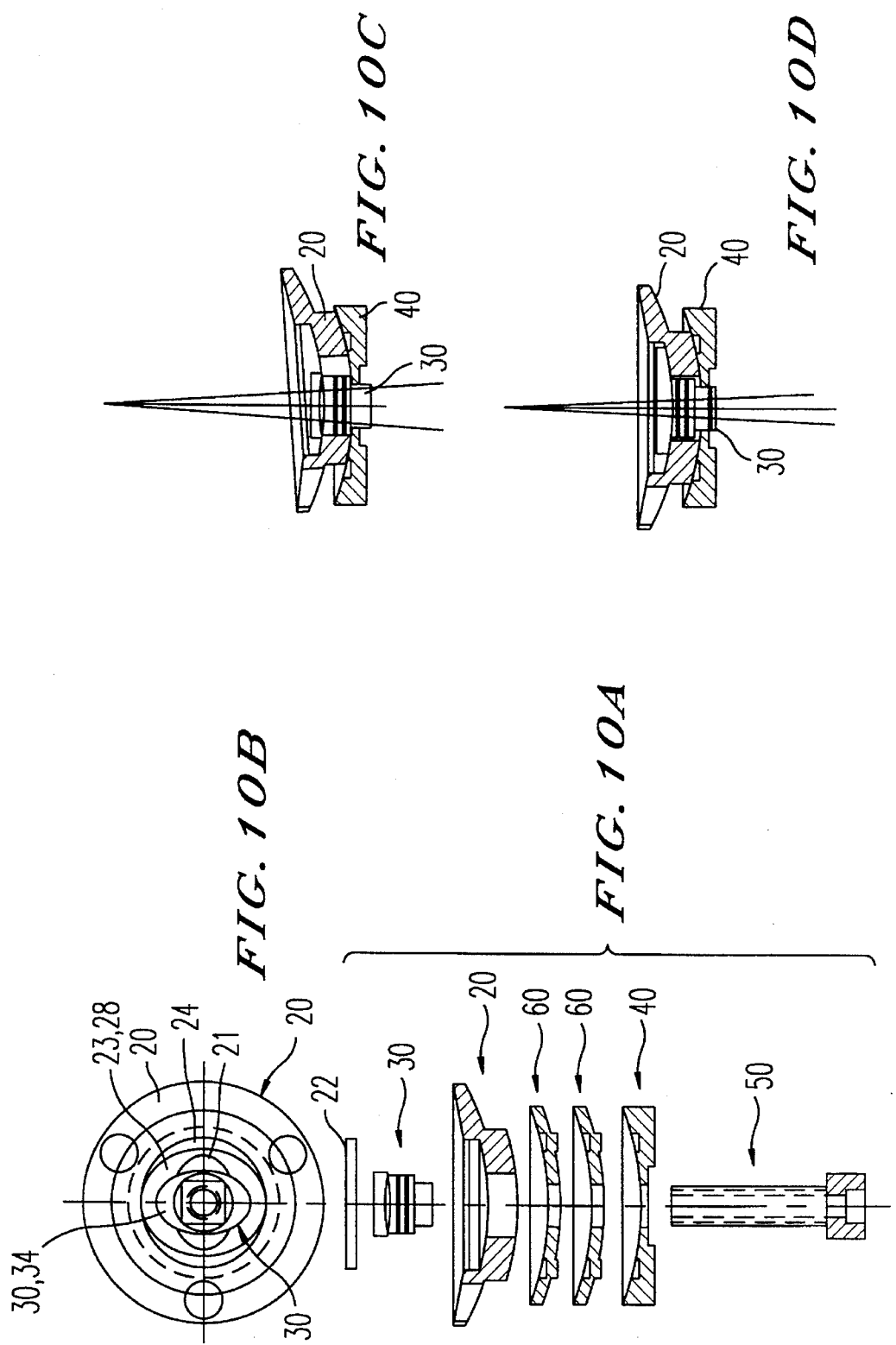

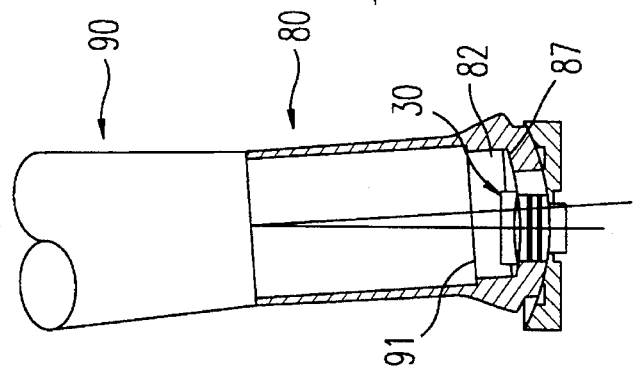
FIG. 11C
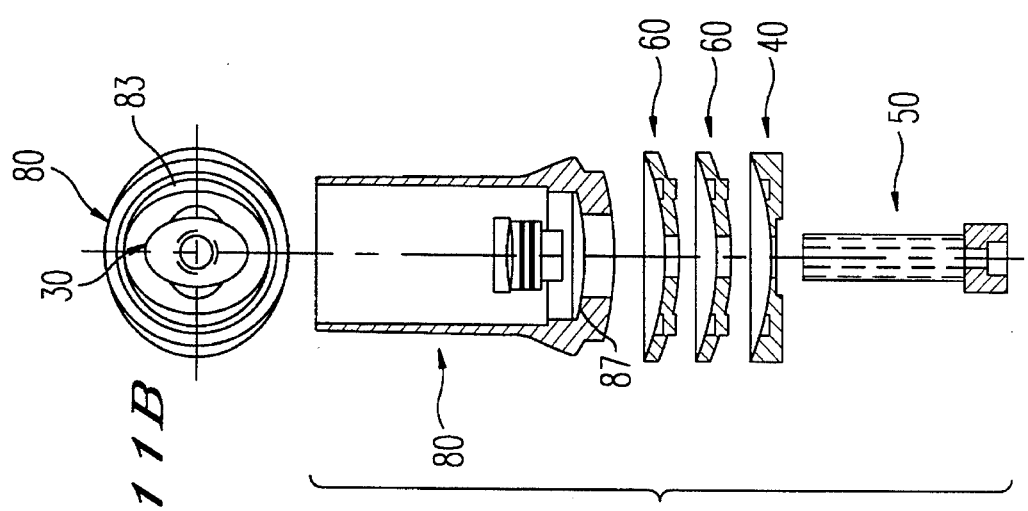
FIG. 11B
FIG. 11A

PROSTHESIS MOUNTING ADAPTER AND METHOD

BACKGROUND OF THE INVENTION

1. Field of the Invention

The invention relates to prosthetic devices, and particularly to an improved adapter and method for facilitating mounting of prosthetic devices, with the device and method particularly advantageous for a Symes amputee.

2. Discussion of the Background

Symes amputation involves the removal of the foot at the ankle. Due to the location of the amputation, it is difficult to build a prosthesis for the Symes amputee while also providing sufficient room for adjusting devices. Traditionally, a Symes prosthesis is fitted by attaching a socket to the stump of the amputee, attaching a Symes nut to the end of the socket in a position which is essentially eyeballed as most appropriate, and then attaching a foot prosthesis to the Symes nut with a bolt. The amputee then walks on the prosthesis to determine whether the foot is properly mounted. If the foot must be moved relative to the socket to obtain an appropriate gait, the bolt can be loosened and toe-out positioning (internal/external rotation) can be adjusted. However, if other adjustments are required (such as inversion/eversion, plantar/dorsiflexion and/or length), the Symes nut must be removed and the foregoing steps of attaching the nut to the end of the socket, attaching of the foot, and trial walking by the amputee are required. Such a trial and error method can be quite time consuming, and often will result in an acceptable, but less than optimal or ideal alignment.

Accordingly, an improved adjusting device is needed which will allow for adjustment of the position and/or orientation of a prosthetic device after the adjustment device is attached to the amputee or a stump socket of the amputee. Further, such a device should be relatively lightweight and require only a small amount of space.

SUMMARY OF THE INVENTION

It is therefore an object of the present invention to provide an improved adapter/mounting device and mounting method for a prosthesis.

It is another object of the present invention to provide a mounting device which is particularly advantageous as an interface between an amputee and a prosthesis such as a prosthetic foot, with the device having small space requirements.

It is a further object of the invention to provide a mounting or adapting device and method for attaching a prosthesis to an amputee, with the device and method particularly advantageous from an adjustability standpoint.

It is a still further object of the present invention to provide a mounting and/or adapter device which is particularly advantageous in fitting a Symes amputee with a prosthesis, and which allows for adjustment after the adapter (or the adapter and prosthetic foot) is attached to the amputee.

These and other objects and advantages are achieved in accordance with the present invention which is particularly advantageous for use as a Symes adapter or, in other words, as a mounting/adjusting device for a prosthesis following a Symes amputation. The adapter and method of the present invention includes providing an interface plate or interface member which is attached to the stump socket, and which includes a movable nut which extends from the interface member. The prosthesis can then be attached to the movable nut utilizing a bolt, such that the position of the prosthesis is clamped in place when the bolt is tightened. The amputee can then test the prosthesis to ensure it is properly oriented and/or positioned. If adjustments are needed, the bolt can be loosened or removed for necessary adjustments, and thereafter, tightened for a subsequent testing by the amputee. Once a desired position and/or orientation is achieved, a resin is injected into a cavity of the interface member within which a head portion of the nut is disposed, such that upon curing of the resin, the assembly is maintained at the desired position. Due to the lightweight and small space requirements of the adapter of the present invention, it is particularly advantageous for a Symes amputee. However, it is to be understood that the present invention may also be utilized for mounting of other prosthetic devices if desired.

BRIEF DESCRIPTION OF THE DRAWINGS

A more complete appreciation of the invention and many of the attendant advantages thereof will become readily apparent from the following detailed description, particularly when considered in conjunction with the drawings in which:

FIG. 1 is a side view of a conventional Symes nut;

FIGS. 2A and 2B are top and side views of a cap component of the Symes adapter of the present invention;

FIGS. 3A and 3B are, respectively, side and bottom views of a nut of the adapter of the present invention;

FIGS. 4A and 4B are top and side cross-sectional views of an interface member;

FIGS. 5A and 5B are top and side cross-sectional views of a height adjuster;

FIGS. 6A–6C are, respectively, top, side cross-sectional and bottom views of a base plate;

FIG. 7 is a side view in partial cross-section of a hollow laminating bolt utilized for injecting a resin into the Symes adapter in accordance with the present invention;

FIGS. 8A and 8B are top and side cross-sectional views of a laminating post for use in a modified form of the present invention;

FIGS. 9A and 9B are side and bottom views of a tooling rod for use in the modified form of the present invention;

FIGS. 10A–10D depict the assembly and adjustability provided by the Symes adapter of the present invention; and FIGS. 11A–11C depict the assembly and adjustability of a modified form of the present invention.

DETAILED DESCRIPTION OF THE PREFERRED EMBODIMENTS

Referring now to the drawings, wherein like reference numerals designate identical or corresponding parts throughout the several views, FIG. 1 shows a conventional Symes nut arrangement. As discussed earlier, the conventional Symes nut 2 is attached to a socket fitted on the stump of the amputee. An upper portion 2a of the nut 2 is attached to the socket of the stump, for example, by an adhesive, and the foot prosthesis is then attached to the Symes nut with a bolt 3. The bolt 3 includes a threaded shaft which is received by an internally threaded portion 2b of the nut 2. The bolt 3 can then be tightened, for example, by an allen wrench which is received in socket 3a.

After a foot is attached to the Symes nut 2 with the bolt 3, the amputee then walks on the prosthesis to determine if the foot has been properly mounted. If a simple internal or external rotation of the foot is needed, the bolt 3 can be loosened and the foot rotated in a toe-in or toe-out direction. However, if other adjustments are required, such as inversion/eversion, plantar/dorsiflexion, and/or length, the Symes nut must be removed and remounted.

The present invention overcomes the shortcomings of the conventional Symes nut mounting arrangement, and provides an adapter which can be adjusted after it is mounted upon a stump or stump socket of an amputee. Referring briefly to FIGS. 10A–10D, the Symes adapter assembly of the present invention includes an interface member 20 which can be attached to a stump socket, for example, by an adhesive in a manner similar to that of the conventional nut 2 of FIG. 1. However, in accordance with the present invention, a movable nut 30 (e.g., of titanium) is partially disposed inside of the interface 20 to allow for positioning after the interface 20 is mounted upon the stump or stump socket. In a preferred form, the interface member includes a cavity which is closed by a cap 22, and which holds a head of the nut such that the head is movable within the cavity. The interface can be formed of composite materials.

A base plate 40 (e.g., of composite materials) is attached to the prosthesis and receives the movable nut 30, such that adjustment of the position and/or orientation of the foot is possible after the foot is mounted upon the amputee. In addition, as discussed in further detail hereinafter, a laminating bolt 50 (e.g., of steel) extends through the foot prosthesis to tighten the assembly at a desired position and allow the user to test walk the prosthetic foot. If adjustments are required, the laminating bolt 50 is loosened and the orientation of the foot is adjusted. Further, spacing of the foot prosthesis with respect to the stump can also be achieved by the addition or removal of optional height adjusters 60 (e.g., of composite materials). Once a desired position is achieved, a resin, such as an acrylic resin, is injected through the laminating bolt 50, such that the resin fills the cavity of the interface 20 to hold the movable nut 30 in place. After the resin hardens or cures, the laminating bolt 50 is preferably removed and replaced with a solid bolt.

As shown in FIGS. 2A and 2B, the cap 22 can be provided in the form of a metal disk, however, other shapes and materials are also possible. The cap 22 closes the cavity or chamber portion of the interface 20 such that the nut 30 is maintained with its head inside of the cavity. Preferably, the cap 22 is attached to the interface 20 with the nut 30 disposed therein by the manufacturer, such that the practitioner responsible for attaching the prosthesis is provided with an interface assembly as a unit including the interface 20, nut 30 and cap 22. The cap 22 can be attached to the interface 20 by an adhesive, by welding, or other known expedients.

As shown in FIGS. 3A and 3B, the nut 30 includes a lower squared first end portion 31. The squared portion 31 can have other shapes, such as hexagonal, etc. However, the portion 31 should have a non-circular cross-section to allow the nut to be locked with respect to other components of the adapter assembly, such as adjustment plate(s) 60 and/or base plate 40 as discussed further hereinafter. The squared portion 31 is locked with respect to the adjustment plates and/or base plate even while adjustments are made, and prior to the final locking of the assembly in place. An intermediate portion 32 of the nut 30 has a circular cross-section, while a head portion 34 has an elliptical cross-section as shown in the 10 drawings. However, it is to be understood that other shapes and configurations may be possible without departing from the teachings of the present invention. Preferably, grooves 33, or a knurled or roughened surface is provided on the nut such that a stronger lamination or bonding is achieved between the nut and the resin (which is injected into the assembly when the final desired positioning is achieved as discussed further hereinafter). In addition, a threaded aperture 36 extends through the nut to mate with a bolt for mounting of the prosthesis. The aperture also allows a resin to be injected through the aperture and into the cavity.

The interface 20 is shown in further detail in FIGS. 4A and 4B. In a preferred form, the interface includes an aperture or opening 21 having an elliptical cross-section as shown in FIG. 4A. The aperture 21 extends into a further apertured portion or cavity 23 which also has an elliptical cross-section, however, the major axis of the elliptical cross-section of the cavity 23 is orthogonal to the major axis of the elliptical cross-section of the aperture 21 (FIG. 4A). In addition, a grooved portion or shelf is provided as shown at 24 to receive the cap 22. The shelf 24 can have a diameter which is the same as the length of the elliptical cross-section of the cavity 23, such that the shelf is provided in the form of a pair of crescent-shaped shelves as shown in FIG. 4A. Of course, the shelf 24 can have a larger diameter, or may have an alternate shape corresponding to an alternate shape of the cap 22.

The second or intermediate portion 32 of the nut is disposed in the aperture 21 (FIG. 10C), and since the elliptical cross-section of the aperture 21 is larger than the circular cross-section of the squared nut, the intermediate portion 32 is movable within the aperture 21. Further, the head 34 of the squared nut is larger than the aperture 21, such that after insertion of the nut 30 into the interface 20 and mounting of the cap 22 upon shelf 24, the head or top portion 34 of the nut is maintained in the cavity 23. Thus, the interface assembly, including the interface 20, cap 22 and nut 30 can be provided to the practitioner such that the interface assembly is mounted upon the stump socket, with the nut movably associated with the interface assembly.

As shown in FIG. 4A, the interface 20 can also include a plurality of apertures 25 on a flanged portion 26 such that when the interface 20 is mounted to a stump socket, for example by an adhesive, the adhesive can enter the apertures 25 for improved adherence of the interface assembly to the stump socket. As shown particularly in FIG. 4B, the flange 26 is preferably cup-shaped or dish-shaped, to provide a desired interface with the stump socket. In other words, the cup-shaped flanged portion 26 is approximately similar to the distal land surface area of a stump socket. Further, as shown in FIG. 4B, the lower surface 27 also includes a curved or convex surface to provide a suitable interface between the interface member 20 and height adjusters 60 or base plate 40 during adjusting and final positioning of the assembly. In a particularly preferred form, the contacting surfaces will have the same radius of curvature (i.e., spherically or three-dimensionally).

FIGS. 5A and 5B show an optional height adjuster 60. As shown particularly in FIG. 5B, the height adjuster 60 also has curved profile, and preferably is meniscus shaped, such that the upper surface 61 can suitably move with respect to the lower surface 27 of the interface, while also being maintained in contact with substantially the entirety of the surface 27 once the final mounting orientation is achieved, regardless of the position. In other words, the height adjuster 60 can be disposed at various positions with respect to the surface 27 as a result of positioning or adjusting movements, while nevertheless maintaining contact with the surface 27 without undesired spacing or canting (which could result in an undesired amount of play in the final assembled condition). It is particularly preferable for the surfaces 27, 61 to have equal radii. In addition, the complementary surfaces 27, 61 of the interface and height adjuster (and base plate as discussed hereinafter), assist in preventing leakage of the resin which will fill the spaces of the cavity 23 and opening 21 once final positioning is achieved. The spacers can impart an additional one-eighth inch spacing to the assembly, however the sizes and number of spacers utilized can be varied.

Preferably, an upper surface of the height adjuster 60 will include a recess or an aperture as shown at 62. In addition, a lower surface of the height adjuster will include a tab or projection 63 which will mate with a corresponding recess or aperture 62 of either an adjacent height adjuster or a base plate 40. Thus, when one or more height adjusters are utilized in combination with a base plate 40, the height adjuster(s) and base plate do not move relative to one another during adjusting movement of the adapter, but rather, the height adjuster(s) and base plate move as a unit with respect to the lower surface 27 of the interface.

As also shown in FIGS. 5A–5B, the height adjuster 60 includes an aperture 64 which corresponds in size and shape to the first portion or lower portion of the nut (squared in the illustrated embodiment). Thus, the height adjuster and base plate will be substantially fixed with respect to the adjusting nut during adjustment of the position of the prosthesis, with the squared or lower portion of the nut received in squared apertures of the height adjusters and/or base plate 40. However, since the nut 30 is movably disposed with respect to the interface 20, the nut 30 and the height adjusters and/or base plate can move with respect to the interface 20.

The base plate 40 is shown in FIGS. 6A–6C. The base plate can be previously mounted upon (or can be formed as part of) a foot prosthesis (or other prosthetic device), or can be mounted onto a prosthesis by the practitioner. As with the height adjusters 60, the base plate includes a squared aperture (or other shape which corresponds to the shape of the lower portion of the nut 30). In addition, recesses 42 are provided in the upper surface of the base plate to receive projections 63 from a height adjuster (when height adjusters are utilized). As with the height adjusters 60, the base plate also has a dished or concave upper surface to (1) receive the height adjusters, and (2) when height adjusters are not utilized, to maintain proper sliding contact with the convex end 27 of the interface 20. Thus, either the height adjuster or the base plate (whichever is in contact with the lower surface 27 of the interface 20) provide a bearing interface with the lower surface 27 of the interface 20. As a result, when the hollow laminating bolt is loosened, the height adjusters or base plate can slide in contact with the lower surface 27, and when the bolt is tightened, the height adjusters and/or base plate are clamped (i.e., between the head of the nut and the head of the bolt) in a fixed position with respect to the interface. This clamped position is sufficient to allow the user to test walk the prosthesis and determine whether the proper position has been achieved. However, since the bolt may loosen after a period of use, once the final position is achieved, a resin is injected into the cavity to secure the final desired position.

As shown in FIG. 7, the laminating bolt 50 includes an externally threaded shaft 51, with a passageway or bore 52 extending through the bolt. In addition, a socket 53 is provided at a head portion of the bolt to allow tightening of the bolt, for example, by an allen wrench. The bore 52 extends from the socket 53 through the bolt such that a filler material, such as an acrylic resin, can be injected through the laminating bolt and into the elliptical cavity portion of the interface which receives the head of the nut, and into the opening 21 which receives the intermediate portion 32 of the nut.

Referring now to FIGS. 10A–D, it will be appreciated that the interface 20 can be attached to a stump socket (with the nut 30 previously inserted into the interface and held therein by cap 22), and the base plate (which is attached to the foot prosthesis) receives the bottom portion of the squared end of the nut. As a result of the size and/or shape of the head 34 and intermediate portion 32 of the nut 30 with respect to the cavity 23 and opening 21, the nut is allowed to move, resulting in sliding contact of the base plate 40 (or base plate and height adjusters when utilized) with the end surface 27 of the interface member, thus allowing movement of the prosthetic foot with respect to the stump after mounting. Further, due to the curved lower surface 34a of the head 34, and the curved lower surface 28 (which is preferably concave or dish-shaped) of the interior of the cavity 23 of the interface, a smooth bearing surface is provided such that a 10 smooth sliding movement is achieved between the lower surface of the nut head and the lower inner surface of the cavity 23 of the interface 20. In a particularly preferred form, the lower surface of the nut head has a radius of the surface 28 within the cavity. In other words, the lower surface of the nut 34a will be a section of a convex surface having the same radius as the concave surface 28 of the cavity 23. In addition, the compatible surfaces of the head and cavity (34a, 28) assist in achieving a strong clamping of the assembly for a test walk.

Although different shapes or geometries can be utilized without departing from the teachings of the present invention, the foregoing described shapes have been found to be particularly advantageous in a number of respects. For example, as discussed earlier, the curved surfaces of the various elements including the base plate 40, height adjusters 60, the lower surface 34a of the nut head 34, and the curved surfaces 27, 28 of the interface allow sliding, bearing-like adjusting movement when the attaching bolt is loosened, while also allowing the elements to be strongly clamped together when the bolt is tightened. In addition, by providing the elliptical aperture 21 in the interface 20, a sufficient area for a good bearing contact (and clamping contact) between the lower surface 34a of the nut head 34 and the lower surface 28 of the cavity 23 is ensured. Moreover, as shown in FIG. 10B, the largest width of the nut head 34 is preferably smaller than the smallest width of the cavity 23. As a result, a complete rotation of the nut within the cavity is not possible, such that the largest width of the nut head 34 can not be aligned with the largest width of the aperture 21 of the interface, thereby ensuring sufficient surface contact of the lower surface of the nut head with the lower surface 28 of the cavity 23. This arrangement also prevents edges or corners of the bottom of the nut head 34 from becoming caught in the aperture 21 of the interface 20. Of course, with the elliptical aperture 21, elliptical head 34 and elliptical cavity 23, differing degrees of freedom are allowed in different directions. FIGS. 10C and 10D show cross-sectional views of the assembly which are orthogonal to one another. As shown in FIG. 10C an 8.0° freedom of movement can be provided with respect to a first direction (which corresponds to the side to side direction in the plan view of FIG. 10B). Further, a 4.0° range of movement is provided in the direction or orthogonal to the direction shown in FIG. 10C, as shown in FIG. 10D (which corresponds to the up and down direction with respect to the plan view shown in FIG. 10B). Thus, the nut 30 is advantageously disposed within the interface 20, and is allowed to rotate and pivot in different directions, with combinations of the movements allowing for optimal positioning of the prosthesis with respect to the stump to which the interface 20 is attached. The orientation of the interface with respect to the stump socket can be varied according to the particular situation or the preferred adjustments desired by a particular practitioner.

As should be apparent from the foregoing, the practitioner will attach the interface assembly 20, including the interface 20, nut 30, and cap 22 to the stump socket, and the prosthetic device will then be attached to the interface utilizing the laminating bolt 50. The prosthesis can then be moved with respect to the stump via the interface assembly, and once a desired position is achieved, the bolt 50 is tightened to clamp the assembly, and prevent further movement. The amputee may then walk upon the prosthesis to determine whether the foot is satisfactorily oriented. If any height adjustment is needed, the bolt 50 is removed, and height adjusters 60 can be added or removed. If internal/external rotation, inversion/eversion, and/or plantar/dorsiflexion adjustments are needed, the hollow laminating bolt is loosened, the position/orientation of the prosthesis is adjusted, and then the hollow laminating bolt is retightened to clamp the prosthesis in place. The user can then test walk the modified position. To ensure that the assembly will not become loose, particularly over a period of use, the laminating bolt 50 is utilized for the injection of a resin material, with the resin material passing through the laminating bolt 50 and through the nut 40 to fill the cavity 23 of the interface 20. Once the resin hardens, a fixed permanent mount is achieved. The hollow laminating bolt 50 can then be replaced with a solid bolt.

Referring now to FIGS. 11A–11C, a modified form of the present invention is shown. The arrangement shown in FIGS. 11A–11C can be utilized, for example, in a "monolithic" prosthesis for a trans-tibia (or below the knee) amputee. As would be readily apparent, many of the features of the arrangement of FIGS. 11A–11C are similar to that shown in FIGS. 10A–10D. However, the interface 20 is replaced with a laminating post 80, shown in further detail in FIGS. 8A and 8B. In addition, the cap 22 is replaced with a tooling rod 90 as shown in FIGS. 9A and 9B. The laminating post 80 can have an elliptical aperture or opening 81 (FIGS. 8A–B) which extends into an elliptical cavity portion 82, with the ellipses orthogonal to one another as with the interface 20 of the embodiment discussed earlier. Further, as with the interface 20, a shelf-like portion 83 is disposed at the top of the cavity 82. The shelves 83 are abutted by a bottom surface 91 of the tooling rod 90 (FIGS. 9A and 9B). The tooling rod includes a larger diameter portion 92 and a smaller diameter portion 93 which is received within the laminating post 80. Thus, a stepped portion is provided as shown at 92a, which is seated upon a top surface 84 of the laminating post. By way of example, and not to be construed as limiting, the upper portion 92 of the tooling rod can have a length $L_1$ of 13.25 inches, with the lower portion 93 having a length $L_2$ of 2.25 inches. Further, the laminating post can have a length $L_3$ of approximately 3 inches.

Thus, as shown in FIGS. 11A–11C, nut 30 is received in the cavity 82, with a lower surface 34a of the nut head 34 in the sliding contact with a bottom, preferably concave, surface 87 of the cavity 82 (and most preferably with the surfaces having equal radii). Thus, rotating, pivoting or rolling types of movement can be achieved as in the previously discussed embodiment. In addition, as in the Symes adapter discussed earlier, once the desired position is achieved, the hollow laminating bolt is utilized to inject a resin into the cavity 82. After the resin has cured, the hollow laminating bolt 50 is removed, and replaced with a solid or permanent bolt.

As should be readily apparent from the foregoing, the present invention provides an adapter and mounting method for attaching a prosthesis, such as a prosthesis for a Symes amputee. The invention is particularly advantageous in allowing for adjustment of the prosthesis after it is mounted, and in allowing for testing of the prosthesis in a clamped position. Once a desired position is achieved, a resin can then be injected into the interface assembly for permanent positioning.

Obviously, numerous modifications and variations of the present invention are possible in view of the above teachings. For example, different forms of connectors could also be utilized, or, the connector associated with the interface member could be provided as a bolt which is attached to a nut opposite to the prosthesis (e.g., with the nut and bolt the reverse of that shown herein). It is therefore to be understood that the invention may be practiced otherwise than as specifically described herein.

What is claimed as new and desired to be secured by Letters Patent of the United States is:

1. An adapter for mounting a prosthesis comprising:
   an interface member having an opening which extends into a cavity; and
   a nut having a first end extending outside of said interface member and a second end including a head disposed inside of said cavity, said nut extending through said opening of said interface member;
   wherein said head of said nut is sized with respect to a size of said cavity such that said head is movable within said cavity; and
   wherein a cross-section of said cavity includes a first cavity width and a second cavity width, and wherein said first cavity width is larger than said second cavity width;
   said head of said nut includes a first head width and a second head width, and wherein said first head width is larger than said second head width, and wherein said first head width is larger than said second cavity width.

2. The adapter of claim 1, further including a base plate which is mounted on a prosthesis, said base plate having an aperture therethrough; and
   wherein said first end of said nut has a cross-sectional shape which corresponds to a shape of said aperture of said base plate, and wherein said first end of said nut extends through said aperture of said base plate.

3. The adapter of claim 2, wherein said interface member includes a convex surface through which said opening extends, and wherein said base plate includes proximate and distal surfaces with said proximate surface facing said convex surface of said interface member, and wherein said proximate surface is concave.

4. The adapter of claim 1, wherein said cavity has an elliptical cross-section and said head of said nut includes an elliptical cross-section.

5. The adapter of claim 1, wherein said cavity includes an elliptical cross-section and said head of said nut includes an elliptical cross-section, and further wherein respective major axes of said elliptical cavity cross-section and said elliptical head cross-section are non-parallel.

6. The adapter of claim 1, wherein said opening of said interface member has an elliptical cross-section.

7. The adapter of claim 6, wherein said cavity includes an elliptical cross-section and a major axis of said elliptical cross-section of said cavity is orthogonal to a major axis of said elliptical cross-section of said opening.

8. The adapter of claim 1, wherein said cavity has a lower surface upon which a lower surface of said head of said nut is in sliding contact.

9. The adapter of claim 8, wherein said lower surface of said cavity is a concave surface, and wherein said lower surface of said nut head is a section of a convex surface, and wherein said concave surface and said convex surface have equal radii.

10. The adapter of claim 1, further including one of:
   (a) a cap enclosing a side of said cavity opposite to a side through which said opening extends; and
   (b) a rod extending into said interface member with an end of said rod enclosing a side of said cavity opposite to a side through which said opening extends.

11. The adapter of claim 1, further including a bolt, said bolt having a threaded shaft, and wherein said nut includes a threaded aperture extending therethrough which receives said threaded shaft, and further wherein said bolt is hollow with a bore extending therethrough for injection of a resin into said cavity.

12. The adapter of claim 1, further including a base plate having an aperture through which said first end of said nut extends, the adapter further including at least one height adjuster plate disposed between said base plate and said interface member, and wherein said height adjuster plate includes an aperture through which said first end of said nut extends.

13. The adapter of claim 12, wherein said base plate includes a concave surface facing toward said interface member, said at least one height adjuster plate having a meniscus shape, and wherein said interface member includes a convex outer surface through which said opening extends.

14. The adapter of claim 1, wherein said nut further includes an intermediate portion disposed between said first end and said head, and wherein said intermediate portion has a cross-sectional shape different from a cross-sectional shape of said first end.

15. The adapter of claim 14, wherein said cross-sectional shape of said intermediate portion is circular, and said cross-sectional shape of said first end of said nut is polygonal.

16. The adapter of claim 15, wherein said opening has an elliptical cross-sectional shape, and wherein said intermediate portion of said nut is disposed in said opening.

17. The adapter of claim 16, wherein said head of said nut has an elliptical cross-sectional shape.

18. The adapter of claim 14, further including a bolt having a threaded shaft, said nut including an aperture extending therethrough at least part of which is threaded to receive the threaded shaft of said bolt; and
   wherein said bolt includes a bore extending therethrough to allow injection of a resin through said bore and through said nut to fill said cavity and said opening.

19. The adapter of claim 1, further including a resin disposed in said cavity.

20. The adapter of claim 1, wherein said nut includes an intermediate portion located between said first end and said head, said intermediate portion disposed in said opening of said interface member, said intermediate portion of said nut being smaller than said opening such that a space is provided between said intermediate portion and a peripheral surface of said opening; and the adapter further including a resin disposed in said cavity and in said space of said opening.

21. The adapter of claim 1, wherein said interface member is a laminating post.

22. The adapter of claim 21, further including a tooling rod which extends into said laminating post.

23. An adapter for mounting a prosthesis comprising:
   an interface member having a cavity;
   a first connector having a first end disposed outside of said interface member and a second end including a head disposed in said cavity, said first connector having an aperture therethrough;
   a second connector which mates with said first conductor at least at said first end of said first connector; and
   a resin disposed through said aperture to at least partially surround said head of said first connector in said cavity.

24. The adapter of claim 23, wherein said first connector is a nut and said second connector is a bolt; and
   said bolt includes a threaded shaft and said nut includes an aperture at least part of which is threaded to mate with the threaded shaft of said bolt, and wherein said bolt includes a bore extending therethrough for injection of said resin into said cavity.

25. The adapter of claim 23, further including a base plate having an aperture through which at least one of said first and second connectors extends.

26. The adapter of claim 25, wherein said base plate includes a curved surface facing said interface member, and said interface member includes a curved surface facing said base plate.

27. The adapter of claim 26, wherein said curved surface of said adapter is a convex surface and said curved surface of said base plate is a concave surface, and wherein said convex surface and said concave surface have equal radii.

28. The adapter of claim 26, wherein said first connector is a nut and said second connector is a bolt.

29. The adapter of claim 28, wherein said head of said first connector has an elliptical cross-section, said first connector further including an intermediate portion disposed between said first end and said head, said intermediate portion disposed in said opening, said intermediate portion including a circular cross-section.

30. The adapter of claim 29, wherein a largest cross-sectional width of the elliptical cross-section of said head is larger than a smallest cross-sectional width of the elliptical cross-section of said cavity.

31. The adapter of claim 30, wherein said second connector is a bolt having a bore extending therethrough for injection of said resin into said cavity.

32. The adapter of claim 26, wherein said head of said nut includes a lower curved surface in contact with a lower surface of said cavity, and wherein said lower surface of said cavity is curved.

33. The adapter of claim 32, wherein said interface member includes:
   an opening extending from said interface member curved surface to said cavity, said opening having an elliptical cross-section; and
   said cavity includes an elliptical cross-section, and wherein a major axis of the elliptical cross-section of the cavity is orthogonal to a major axis of the elliptical cross-section of said opening.

34. The adapter of claim 23, wherein said interface member is a laminating post.

35. The adapter of claim 34, further including a tooling rod which extends into said laminating post.

36. An adapter for mounting a prosthesis comprising:

an interface member having an opening, and wherein said interface member includes an inner curved surface partially delimiting a cavity, said opening extending through said inner curved surface;

a nut having a first end extending outside of said interface member and a second end including a head disposed inside of said cavity, said first end of said nut including a non-circular cross-sectional shape, said nut extending through said opening of said interface member;

a base plate having an aperture therethrough, said aperture having a same shape as said non-circular cross-sectional shape of said first end of said nut, and wherein said non-circular cross-sectional shape of said first end of said nut is disposed in said aperture; and wherein said head of said nut is sized with respect to a size of said cavity such that said head is movable within said cavity, and wherein said head of said nut includes a lower curved surface integrally attached to said head, in sliding contact with said inner curved surface of said interface member through which said opening extends, and further wherein a stem of said nut extends from said curved surface of said nut, said stem including said first end of said nut.

37. The adapter of claim 36, wherein said head of said nut has an elliptical cross-section and said cavity has an elliptical cross-section.

38. The adapter of claim 36, wherein said interface member is a laminating post.

39. The adapter of claim 38, further including a tooling rod which extends into said laminating post.

40. The adapter of claim 36, wherein said interface member further includes an outer surface through which said opening extends, and wherein said outer surface is curved.

* * * * *